United States Patent [19]
Kasai et al.

[11] Patent Number: 5,350,769
[45] Date of Patent: Sep. 27, 1994

[54] ANTIINFLAMMATORY GEL PREPARATION

[75] Inventors: Shuichi Kasai; Yasuo Ikeda; Satoru Enomoto, all of Narita; Katsumi Imamori; Akira Iwasa, both of Yotsukaido, all of Japan

[73] Assignee: SS Pharmaceutical Co., Ltd., Tokyo, Japan

[21] Appl. No.: 835,979

[22] PCT Filed: Oct. 30, 1990

[86] PCT No.: PCT/JP90/01392
§ 371 Date: May 14, 1993
§ 102(e) Date: May 14, 1993

[87] PCT Pub. No.: WO92/07561
PCT Pub. Date: May 14, 1992

[51] Int. Cl.$^5$ .............................................. A61K 31/19
[52] U.S. Cl. ................... 514/567; 514/772.2; 514/781; 514/785; 514/946; 514/947
[58] Field of Search ...................... 514/567, 772.2, 781, 514/785, 946, 947

[56] References Cited
U.S. PATENT DOCUMENTS

| | | | |
|---|---|---|---|
| 4,746,675 | 5/1988 | Makino et al. | 514/423 |
| 4,873,081 | 10/1989 | Ogiso | 424/81 |
| 5,030,629 | 7/1991 | Rajadhyaksha | 514/211 |
| 5,039,513 | 8/1991 | Chatterjee et al. | 424/47 |

FOREIGN PATENT DOCUMENTS 62-263122 11/1987 Japan.
63-287721 11/1988 Japan.
1-250313 10/1989 Japan.
2-49722 2/1990 Japan.

Primary Examiner—Marianne M. Cintins
Assistant Examiner—William R. A. Jarvis
Attorney, Agent, or Firm—Oblon, Spivak, McClelland, Maier & Neustadt

[57] ABSTRACT

The present invention relates to an antiinflammatory gel preparation comprising an ammonium or sodium salt of diclofenac, a nonionic polymer, a dibasic ester, and a lower alcohol. The gel preparation of the present invention exhibits superior percutaneous absorptivity, thus providing sufficient medical effects of the two diclofenac salts. In addition, the preparation is stable over time even at a high concentration of the diclofenac salts.

5 Claims, 4 Drawing Sheets

ANTIINFLAMMATORY GEL PREPARATION

FIELD OF THE INVENTION

The present invention relates to an antiinflammatory gel preparation which can contain diclofenac or a salt thereof a high concentration and which exhibits superior stability and excellent percutaneous absorptivity.

DESCRIPTION OF THE BACKGROUND ART

Diclofenac or its salts possess excellent antiinflammatory action, and are widely used in clinics with oral and rectal dosage form. When administered orally or rectally, they are known to cause various side effects, including gastrointestinal tract disturbance. Because of this reason, a preparation for external application has been proposed, by which the drug is percutaneously absorbed without going through gastrointestinal tract and exhibits its action locally or systemically. However, since diclofenac and its salts are scarcely absorbed percutaneously, such a preparation has not been commercially sold.

Gel preparations, on the other hand, possess an advantage over other preparations for external application in terms of the good feeling upon use. When a gel preparation contains diclofenac or its salts as an active ingredient there are problems that a high concentration of diclofenac or its salts may destruct the gel structure, liquefying the gel or crystallizing over time.

In view of this situation the present inventors have undertaken extensive studies and found that if base components comprising a dibasic ester and a lower alcohol are gelatinized by using a nonionic polymer as a gelling agent, diclofenac or its salts can be contained at a high concentration and in a stable manner, providing gel preparations with excellent percutaneous absorptivity. The finding has led to the completion of the present invention.

DISCLOSURE OF THE INVENTION

The present invention provides an antiinflammatory gel preparation characterized by comprising diclofenac or its salts, a nonionic polymer, a dibasic ester, and a lower alcohol.

BEST MODE FOR IMPLEMENTING THE INVENTION

Figure 1:
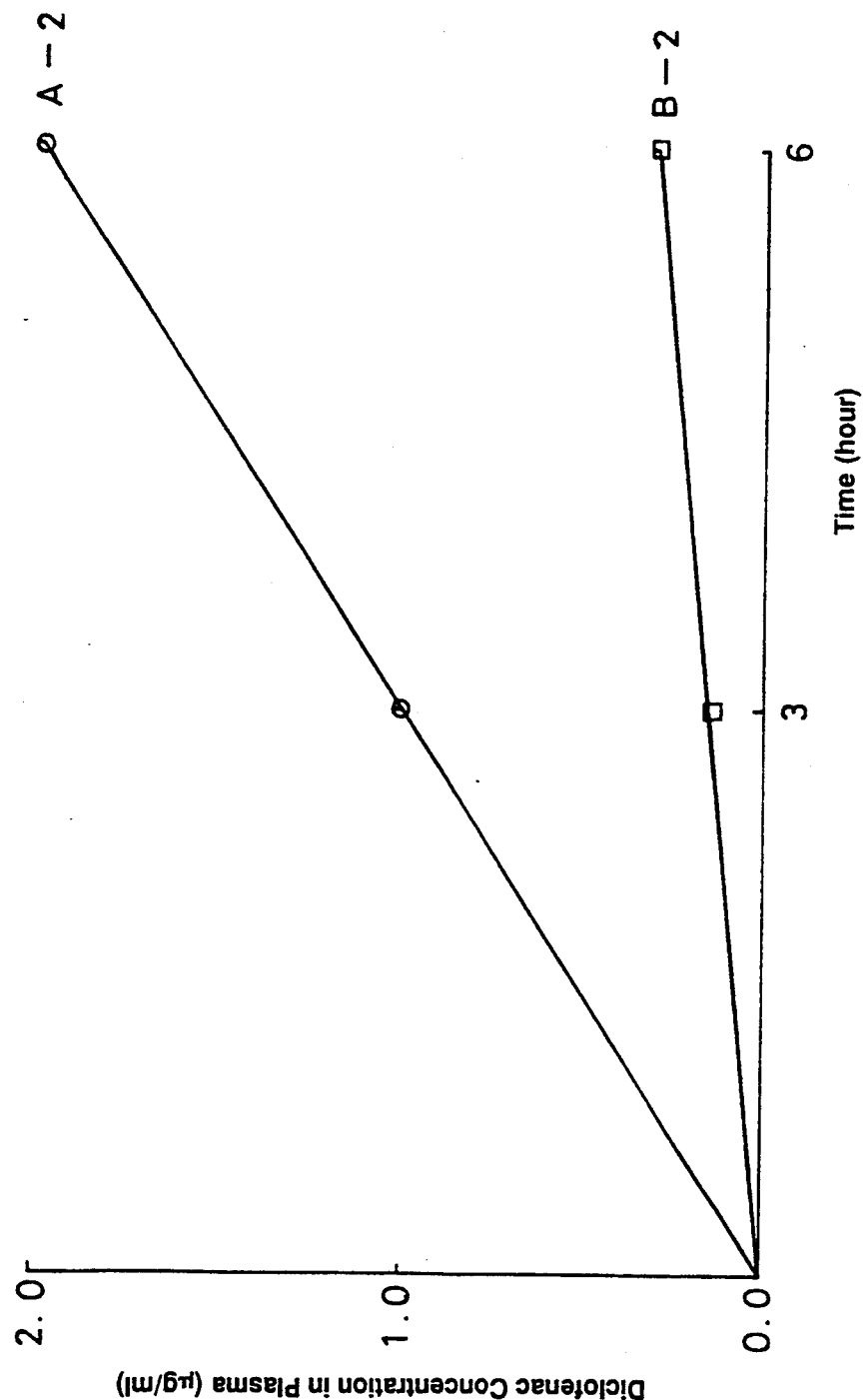
FIG. 1 shows a comparison of plasma concentration of dicrofenac after abdominal administration of gel ointments A-2 and B-2 in rats.

There are no specific restrictions as to the salts of diclofenac, so long as they are pharmaceutically acceptable compounds. Given as examples of such salts are salts of alkali metal, alkaline earth metal, ammonia, and primary, secondary, or tertiary alkanolamine; e.g., sodium, potassium, calcium, ammonium, dimethylamine, diethylamine, trimethylamine, triethylamine, monoethanolamine, diethanolamine, diisopropanolamine, triethanolamine, triisopropanolamine, and the like. Especially preferable salts are sodium salts and ammonium salts. There are no limitations to the amount of diclofenac or its salts in the preparation; it may be the amount by which the medicinal effect is exhibited. Generally, an amount of 0.1–20%, especially 0.5–10%, is preferable.

A nonionic polymer is an important component of the present invention. The gel preparation comprising diclofenac or its salts can be obtained without destructing the gel structure by using a nonionic polymer as a gelling agent. In addition, the nonionic polymer enables the preparation to include a large amount of lower alcohol which helps to promote the percutaneous absorption of diclofenac or its salts and to enhance their dissolution into the base components. Examples of nonionic polymers which can be given are those capable of forming a gel in a mixed solution of an ester of dibasic acid, a lower alcohol and water; e.g., ethylcellulose, hydroxyethylmethyl cellulose, hydroxypropyl cellulose, hydroxypropylmethyl cellulose, hydroxymethyl cellulose, hydroxyethyl cellulose, polyvinyl pyrrolidone, polyvinyl alcohol, methylcellulose, and the like. They may be used either individually or in combination of two or more. Of these, the combined use of hydroxyethyl cellulose and hydroxypropyl cellulose is preferable.

The amount of a nonionic polymer incorporated into the composition depends on the types of the nonionic polymer, and further the type and the amount of diclofenac or its salt, an ester of dibasic acid, and a lower alcohol to be used. Generally, the amount of 0.5–20%, especially 1–10%, is preferable.

As esters of dibasic acid, those dissolvable in a mixed solvent of a lower alcohol and water and capable of promoting the percutaneous permeability of diclofenac or its salts are preferable. Specific examples are diisopropyl adipate, diisopropyl sebacate, and diethyl sebacate. They may be either used individually, or two or more of them together. The amount of esters of dibasic acid to be incorporated should be sufficient to achieve the desired absorption of diclofenac or its salts. Generally, the amount of 0.5–15%, especially 1.5–10%, is preferable.

Any lower alcohols which are pharmaceutically acceptable may be used without specific limitation. Examples which may be given include ethyl alcohol, isopropyl alcohol, and a mixture of these. The amount of lower alcohol to be incorporated into the preparation varies depending on the types of nonionic polymer, pH of the preparation, types and amount of diclofenac or its salts and other liquid components. Generally, the amount of 10–80%, especially 25–70%, is preferable.

If the pH of the gel preparation of the present invention is in extremely basic or acidic side, its repeated application to the same site may cause changes in the percutaneous absorption of diclofenac or its salts or may give undesirable adverse side effects on the human body such as irritation to the skin. Furthermore, since the solubility of diclofenac or its salts in a solvent is affected by its pH, the change of pH may cause diclofenac or its salts to crystallize over time. Because of these reasons, it is desirable to add a pH modifier to the preparation of the present invention to adjust its pH in the range of 5–8.5, preferably 5.5–8. There are no specific limitations as to the kind of the pH modifier inasmuch as the same is capable of adjusting the pH within the above range. Given as examples of such pH modifiers are inorganic pH modifiers, e.g., hydrochloric acid, sodium hydroxide, and potassium hydroxide; and organic acids, e.g., acetic acid, lactic acid, citric acid, malic acid, tartaric acid, maleic acid, fumaric acid, adipic acid, salicylic acid, and the like, as well as their salts. They may be used either individually, or two or more of them may be together. Furthermore, an acidic pH modifier and basic pH modifier may be used together to provide a buffering effect.

There are no specific limitations to the method of preparing the preparation of the present invention. Generally, a preferable method comprises mixing of liquid components, addition of diclofenac or its salts to the mixture to dissolve it thereinto, adjustment of pH by the addition of the pH modifier, followed by the addition of the nonionic polymer slowly while stirring to obtain a gel preparation. Other methods may be employed conforming to the characteristics of the gel formulation, equipment to be used, and the like. To the preparation of the present invention, may optionally be added moisturizing agents, solubilizers, stabilizers, perfumes, coloring agents, and the like; and if required for improving the feeling upon use, may further be added other components which are commonly used in external dosage forms such as surface active agents, urea, methyl salicylate, crotamiton, menthol, and the like.

EXAMPLES

The present invention is illustrated in more detail by way of Examples.

Example 1

Isopropyl alcohol, diisopropyl adipate, and a portion of purified water were mixed, and to the solution was dissolved diclofenac sodium, and then were added hydroxyethyl cellulose and hydroxypropyl cellulose. After stirring to homogeneous state, the mixture was adjusted to about pH 7 with lactic acid. The remaining purified water was added to make total volume 100 g to obtain compositions shown in Table 1.

TABLE 1

|  | A-1 | A-2 | A-3 | A-4 | A-5 | A-6 |
|---|---|---|---|---|---|---|
| Diclofenac sodium | 0.5 g | 1.0 g | 2.0 g | 3.0 g | 5.0 g | 10.0 g |
| Diisopropyl adipate | 5.0 | 5.0 | 5.0 | 5.0 | 5.0 | 5.0 |
| Isopropyl alcohol | 40.0 | 40.0 | 40.0 | 40.0 | 40.0 | 40.0 |
| Hydroxyethyl cellulose | 1.0 | 1.0 | 1.0 | 1.0 | 1.0 | 1.0 |
| Hydroxypropyl cellulose | 1.0 | 1.0 | 1.0 | 1.0 | 1.0 | 1.0 |
| Lactic acid | q.s. | q.s. | q.s. | q.s. | q.s. | q.s. |
| Purified water | q.s. | q.s. | q.s. | q.s. | q.s. | q.s. |
| Total amount | 100.0 g | 100.0 g | 100.0 g | 100.0 g | 100.0 g | 100.0 g |

Comparative Example 1

Diclofenac sodium was dissolved into a mixed solvent of propylene glycol and isopropyl alcohol. To the solution was added carboxyvinyl polymer which had been swelled in a portion of purified water. After stirring, the mixture was adjusted to pH 7 with aqueous ammonia. The remaining purified water was added to make total volume 100 g to obtain compositions shown in Table 2.

TABLE 2

|  | B-1 | B-2 | B-3 | B-4 |
|---|---|---|---|---|
| Diclofenac sodium | 0.5 g | 1.0 g | 2.0 g | 3.0 g |
| Propylene glycol | 5.0 | 5.0 | 5.0 | 5.0 |
| Isopropyl alcohol | 20.0 | 20.0 | 20.0 | 20.0 |
| Carboxyvinyl polymer | 2.0 | 2.0 | 2.0 | 2.0 |
| Aqueous ammonia | q.s. | q.s. | q.s. | q.s. |
| Purified water | q.s. | q.s. | q.s. | q.s. |
| Total amount | 100.0 g | 100.0 g | 100.0 g | 100.0 g |

Test Example 1

The appearances of compositions prepared in Example 1 and Comparative Example 1 were observed to compare the conditions of the gels. The results are shown in Table 3.

TABLE 3

|  | Content of diclofenac sodium (w/w %) | Gel Conditions |
|---|---|---|
| Example 1 |  |  |
| A-1 | 0.5 | O |
| A-2 | 1.0 | O |
| A-3 | 2.0 | O |
| A-4 | 3.0 | O |
| A-5 | 5.0 | O |
| A-6 | 10.0 | O |
| Comparative Example 1 |  |  |
| B-1 | 0.5 | O |
| B-2 | 1.0 | O |
| B-3 | 2.0 | X |
| B-4 | 3.0 | X |

O: Gel conditions were excellent
X: Liquefied due to destruction of the gel

As demonstrated by Table 3, the gel ointments of the present invention can contain diclofenac sodium at a high concentration.

Example 2

Composition of Table 4 were prepared in the same manner as in Example 1.

TABLE 4

|  | A-7 | A-8 | A-9 |
|---|---|---|---|
| Diclofenac sodium | 1.0 g | 1.0 g | 1.0 g |
| Diisopropyl adipate | 5.0 | 5.0 | 5.0 |
| Isopropyl alcohol | 40.0 | 50.0 | 60.0 |
| Hydroxyethyl cellulose | 1.0 | 1.0 | 1.0 |
| Hydroxypropyl cellulose | 1.0 | 1.0 | 1.0 |
| Lactic acid | q.s. | q.s. | q.s. |
| Purified water | q.s. | q.s. | q.s. |
| Total amount | 100.0 g | 100.0 g | 100.0 g |

Comparative Example 2

Composition of Table 5 were prepared in the same manner as in Comparative Example 1.

TABLE 5

|  | B-5 | B-6 | B-7 |
|---|---|---|---|
| Diclofenac sodium | 1.0 g | 1.0 g | 1.0 g |
| Propylene glycol | 5.0 | 5.0 | 5.0 |
| Isopropyl alcohol | 20.0 | 30.0 | 40.0 |
| Carboxyvinyl polymer | 2.0 | 2.0 | 2.0 |
| Aqueous ammonia | q.s. | q.s. | q.s. |
| Purified water | q.s. | q.s. | q.s. |
| Total amount | 100.0 g | 100.0 g | 100.0 g |

Comparative Example 3

Diclofenac sodium was dissolved into a mixed solvent of propylene glycol and isopropyl alcohol. To the solution was added sodium carboxymethyl cellulose which had been swelled in a portion of purified water. After stirring, the mixture was adjusted to about pH 7 with aqueous ammonia. The remaining purified water was added to make total volume 100 g to obtain compositions shown in Table 6.

TABLE 6

|  | B-8 | B-9 | B-10 |
| --- | --- | --- | --- |
| Diclofenac sodium | 1.0 g | 1.0 g | 1.0 g |
| Propylene glycol | 5.0 | 5.0 | 5.0 |
| Isopropyl alcohol | 20.0 | 30.0 | 40.0 |
| Sodium carboxymethyl cellulose | 2.0 | 2.0 | 2.0 |
| Lactic acid | q.s. | q.s. | q.s. |
| Purified water | q.s. | q.s. | q.s. |
| Total amount | 100.0 g | 100.0 g | 100.0 g |

Test Example 2

The appearances of compositions prepared in Examples 2 and Comparative Examples 2 and 3 were observed to compare the conditions of the gels. The results are shown in Table 7.

TABLE 7

|  | Content of isopropyl alcohol (w/w %) | Gel Conditions |
| --- | --- | --- |
| Example 2 |  |  |
| A-7 | 40 | O |
| A-8 | 50 | O |
| A-9 | 60 | O |
| Comparative Example 2 |  |  |
| B-5 | 20 | O |
| B-6 | 30 | Y |
| B-7 | 40 | X |
| Comparative Example 3 |  |  |
| B-8 | 20 | O |
| B-9 | 30 | Y |
| B-10 | 40 | X |

O: Gel conditions were excellent
Y: Softened due to destruction of the gel
X: Liquefied due to destruction of the gel As shown in Table 7, the gel ointments of the present invention not only improve the feeling upon use but also contain a large amount of lower alcohol which can enhance the percutaneous absorption of diclofenac or its salts.

Example 3

Compositions of Tables 8 and 9 were prepared in the same manner as in Example 1.

TABLE 8

|  | A-10 | A-11 | A-12 |
| --- | --- | --- | --- |
| Diclofenac sodium | 1.0 g | 1.0 g | 1.0 g |
| Diisopropyl adipate | 0.5 | 1.0 | 1.5 |
| Isopropyl alcohol | 25.0 | 25.0 | 25.0 |
| Hydroxyethyl cellulose | 1.0 | 1.0 | 1.0 |
| Hydroxypropyl cellulose | 1.0 | 1.0 | 1.0 |
| Lactic acid | q.s. | q.s. | q.s. |
| Purified water | q.s. | q.s. | q.s. |
| Total amount | 100.0 g | 100.0 g | 100.0 g |

TABLE 9

|  | A-13 | A-14 | A-15 | A-16 | A-17 | A-18 |
| --- | --- | --- | --- | --- | --- | --- |
| Diclofenac sodium | 1.0 g | 1.0 g | 1.0 g | 1.0 g | 1.0 g | 1.0 g |
| Diisopropyl adipate | 2.0 | 3.0 | 4.0 | 5.0 | 7.0 | 10.0 |
| Isopropyl alcohol | 40.0 | 40.0 | 40.0 | 40.0 | 40.0 | 40.0 |
| Hydroxyethyl cellulose | 1.0 | 1.0 | 1.0 | 1.0 | 1.0 | 1.0 |
| Hydroxypropyl cellulose | 1.0 | 1.0 | 1.0 | 1.0 | 1.0 | 1.0 |
| Lactic acid | q.s. | q.s. | q.s. | q.s. | q.s. | q.s. |
| Purified water | q.s. | q.s. | q.s. | q.s. | q.s. | q.s. |
| Total amount | 100.0 g | 100.0 g | 100.0 g | 100.0 g | 100.0 g | 100.0 g |

Test Example 3

The appearances of compositions prepared in Examples 3 were observed to compare the conditions of the gels. The results are shown in Table 10.

TABLE 10

|  | Content of isopropyl alcohol (w/w %) | Content of diisopropyl adipate (w/w %) | Gel Conditions |
| --- | --- | --- | --- |
| A-10 | 25 | 0.5 | O |
| A-11 | 25 | 1 | O |
| A-12 | 25 | 1.5 | O |
| A-13 | 40 | 2 | O |
| A-14 | 40 | 3 | O |
| A-15 | 40 | 4 | O |
| A-16 | 40 | 5 | O |
| A-17 | 40 | 7 | O |
| A-18 | 40 | 10 | O |

O: Transparent or slightly turbid
X: Turbid in white

As shown in Table 10, since the gel ointments of the present invention can contain a large amount of lower alcohol, the amount of esters of dibasic acid to be incorporated which have an enhancement effect of promoting percutaneous absorption of declofenac or its salt, may easily be adjusted. Thus, along with percutaneous absorption enhancement effect of lower alcohol, the percutaneous absorption of diclofenac or its salts from the gel ointment of the present invention can be controlled.

Example 4

Gel ointment A-19 of the present invention was prepared in the same manner as in Example 1.

| Diclofenac sodium | 1.0 g |
| --- | --- |
| Diisopropyl adipate | 3.0 |
| Isopropyl alcohol | 30.0 |
| Hydroxyethyl cellulose | 1.0 |
| Hydroxypropyl cellulose | 1.0 |
| Lactic acid | q.s. |
| Purified water | q.s. |
| Total | 100.0 g |

Example 5

Isopropyl alcohol, diisopropyl adipate, and a portion of purified water were mixed, and to the solution was dissolved diclofenac sodium, and then were added hydroxyethyl cellulose and hydroxypropyl cellulose. After stirring to homogeneous state, the mixture was adjusted to about pH 7 with citric acid. The remaining purified water was added to make total volume 100 g to obtain gel ointment A-20 of the present invention.

| Diclofenac sodium | 1.0 g |
|---|---|
| Diisopropyl adipate | 5.0 |
| Isopropyl alcohol | 40.0 |
| Hydroxyethyl cellulose | 1.0 |
| Hydroxypropyl cellulose | 1.0 |
| Citric acid | q.s. |
| Purified water | q.s. |
| Total | 100.0 g |

Example 6

Isopropyl alcohol, diethyl sebacate, and a portion of purified water were mixed, and to the solution was dissolved diclofenac sodium, and then was added hydroxypropyl cellulose. After stirring to homogeneous state, the mixture was adjusted to about pH 7 with tartaric acid. The remaining purified water was added to make the total volume 100 g to obtain gel ointment A-21 of the present invention.

| Diclofenac sodium | 1.0 g |
|---|---|
| Diethyl sebacate | 3.0 |
| Isopropyl alcohol | 40.0 |
| Hydroxypropyl cellulose | 2.5 |
| Tartaric acid | q.s. |
| Purified water | q.s. |
| Total | 100.0 g |

Example 7

Ethyl alcohol, diisopropyl adipate, and a portion of purified water were mixed, and to the solution was dissolved diclofenac ammonium, and then was added hydroxypropyl cellulose. After stirring to homogeneous state, the mixture was adjusted to about pH 7 with citric acid. The remaining purified water was added to make the total volume 100 g to obtain gel ointment A-22 of the present invention.

| Diclofenac ammonium | 1.5 g |
|---|---|
| Diisopropyl adipate | 4.0 |
| Ethanol | 40.0 |
| Hydroxypropyl cellulose | 2.5 |
| Citric acid | q.s. |
| Purified water | q.s. |
| Total | 100.0 g |

Example 8

Isopropyl alcohol, diisopropyl adipate, and a portion of purified water were mixed, and to the solution was dissolved diclofenac, and then were added hydroxyethyl cellulose and hydroxypropyl cellulose. After stirring to homogeneous state, the mixture was adjusted to about pH 7 with 10% aqueous solution of sodium hydroxide. The remaining purified water was added to make the total volume 100 g to obtain gel ointment A-23 of the present invention.

| Diclofenac | 1.0 g |
|---|---|
| Diisopropyl adipate | 5.0 |
| Isopropyl alcohol | 40.0 |
| Hydroxyethyl cellulose | 1.0 |
| Hydroxypropyl cellulose | 1.0 |
| 10% Sodium hydroxide | q.s. |
| Purified water | q.s. |
| Total | 100.0 g |

Example 9

Isopropyl alcohol, diisopropyl adipate, and a portion of purified water were mixed, and to the solution was dissolved diclofenac sodium, and then was added polyvinyl alcohol. After stirring to homogeneous state, the mixture was adjusted to about pH 7 with citric acid. The remaining water was added to make the total volume 100 g to obtain gel ointment A-24 of the present invention.

| Diclofenac sodium | 1.0 g |
|---|---|
| Diisopropyl adipate | 1.0 |
| Isopropyl alcohol | 25.0 |
| Polyvinyl alcohol | 10.0 |
| Citric acid | q.s. |
| Purified water | q.s. |
| Total | 100.0 g |

Example 10

Isopropyl alcohol, diisopropyl adipate, and a portion of purified water were mixed, and to the solution was dissolved diclofenac sodium, and then was added hydroxypropylmethyl cellulose. After stirring to homogeneous state, the mixture was adjusted to about pH 7 with lactic acid. The remaining purified water was added to make the total volume 100 g to obtain gel ointment A-25 of the present invention.

| Diclofenac sodium | 1.0 g |
|---|---|
| Diisopropyl adipate | 5.0 |
| Isopropyl alcohol | 40.0 |
| Hydroxypropylmethyl cellulose | 2.0 |
| Lactic acid | q.s. |
| Purified water | q.s. |
| Total | 100.0 g |

Example 11

Isopropyl alcohol, diisopropyl adipate, and a portion of purified water were mixed, and to the solution was dissolved diclofenac sodium, and then was added methyl cellulose. After stirring to homogeneous state, the mixture was adjusted to about pH 7 with lactic acid. The remaining purified water was added to make the total volume 100 g to obtain gel ointment A-26 of the present invention.

| Diclofenac sodium | 1.0 g |
|---|---|
| Diisopropyl adipate | 5.0 |
| Isopropyl alcohol | 40.0 |
| Methylcellulose | 2.0 |
| Lactic acid | q.s. |
| Purified water | q.s. |
| Total | 100.0 g |

Example 12

Isopropyl alcohol, diisopropyl adipate, and a portion of purified water were mixed, and to the solution was dissolved diclofenac sodium, and then were added ethylcellulose and hydroxypropyl cellulose. After stirring to homogeneous state, the mixture was adjusted to about pH 7 with lactic acid. The remaining purified water was added to make the total volume 100 g to obtain gel ointment A-27 of the present invention.

| | |
|---|---|
| Diclofenac sodium | 1.0 g |
| Diisopropyl adipate | 5.0 |
| Isopropyl alcohol | 70.0 |
| Ethylcellulose | 5.0 |
| Hydroxypropyl cellulose | 1.0 |
| Lactic acid | q.s. |
| Purified water | q.s. |
| Total | 100.0 g |

Example 13

Isopropyl alcohol, diisopropyl adipate, and a portion of purified water were mixed, and to the solution was dissolved diclofenac sodium, and then were added polyvinyl pyrrolidone and hydroxypropyl cellulose. After stirring to homogeneous state, the mixture was adjusted to about pH 7 with lactic acid. The remaining purified water was added to make the total volume 100 g to obtain gel ointment A-28 of the present invention.

| | |
|---|---|
| Diclofenac sodium | 1.0 g |
| Diisopropyl adipate | 5.0 |
| Isopropyl alcohol | 40.0 |
| Polyvinyl pyrrolidone | 7.0 |
| Hydroxypropyl cellulose | 1.0 |
| Lactic acid | q.s. |
| Purified water | q.s. |
| Total | 100.0 g |

Test Example 4

Percutaneous absorption of diclofenac was examined on groups of rats, 3 rats per group, by using as samples gel ointment A-2 of the present invention obtained in Example 1, and gel ointment B-2 obtained in Comparative Example 1. 0.5 g of each sample was applied to the hair-shaved abdomen of rats by the occlusive dressing technique, and the diclofenac concentrations in plasma were measured by HPLC 3 and 6 hours after the application. The results are shown in FIG. 1, which demonstrates excellent percutaneous absorption of declofenac from gel ointments of the present invention.

Test Example 5

Figure 2:
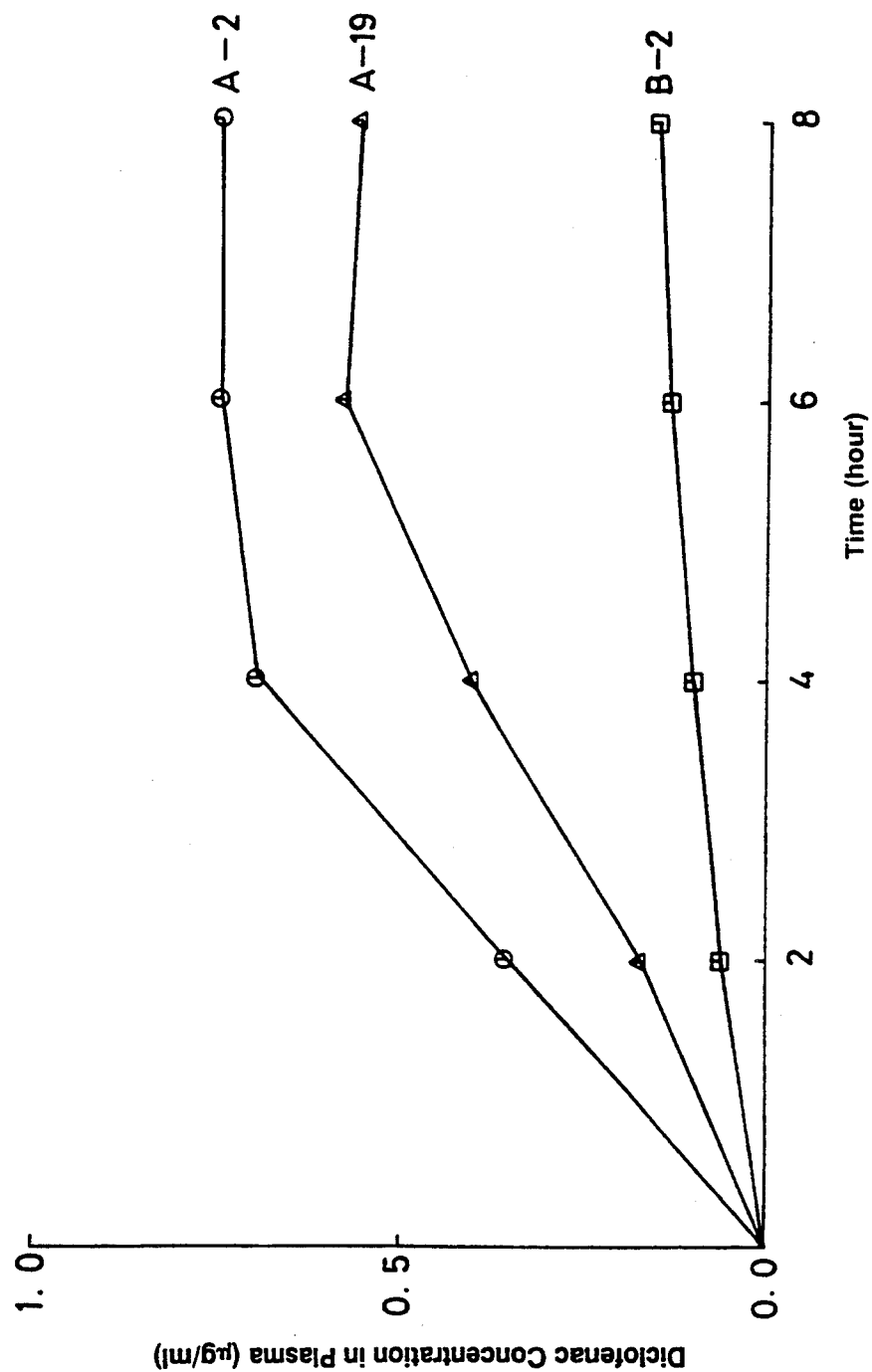
FIG. 2 shows a comparison of plasma concentration of decrofenac after administration of gel ointments A-2, A-19, and B-2 in the back of guinea pigs.

Percutaneous absorption of diclofenac was examined on groups of guinea pigs, each group consisting of 3 guinea pigs, by using as samples gel ointment A-2 of the present invention obtained in Example 1, gel ointment A-19 of the present invention obtained in Example 4, and gel ointment B-2 obtained in Comparative Example 1. 1 g of each sample was applied to the hair-shaved back of guinea pigs by the occlusive dressing technique, and the diclofenac concentrations in plasma were measured by HPLC 2, 4, 6 and 8 hours after the application. The results are shown in FIG. 2, which demonstrates excellent percutaneous absorption of diclofenac from gel ointments of the present invention.

Test Example 6

Figure 3:
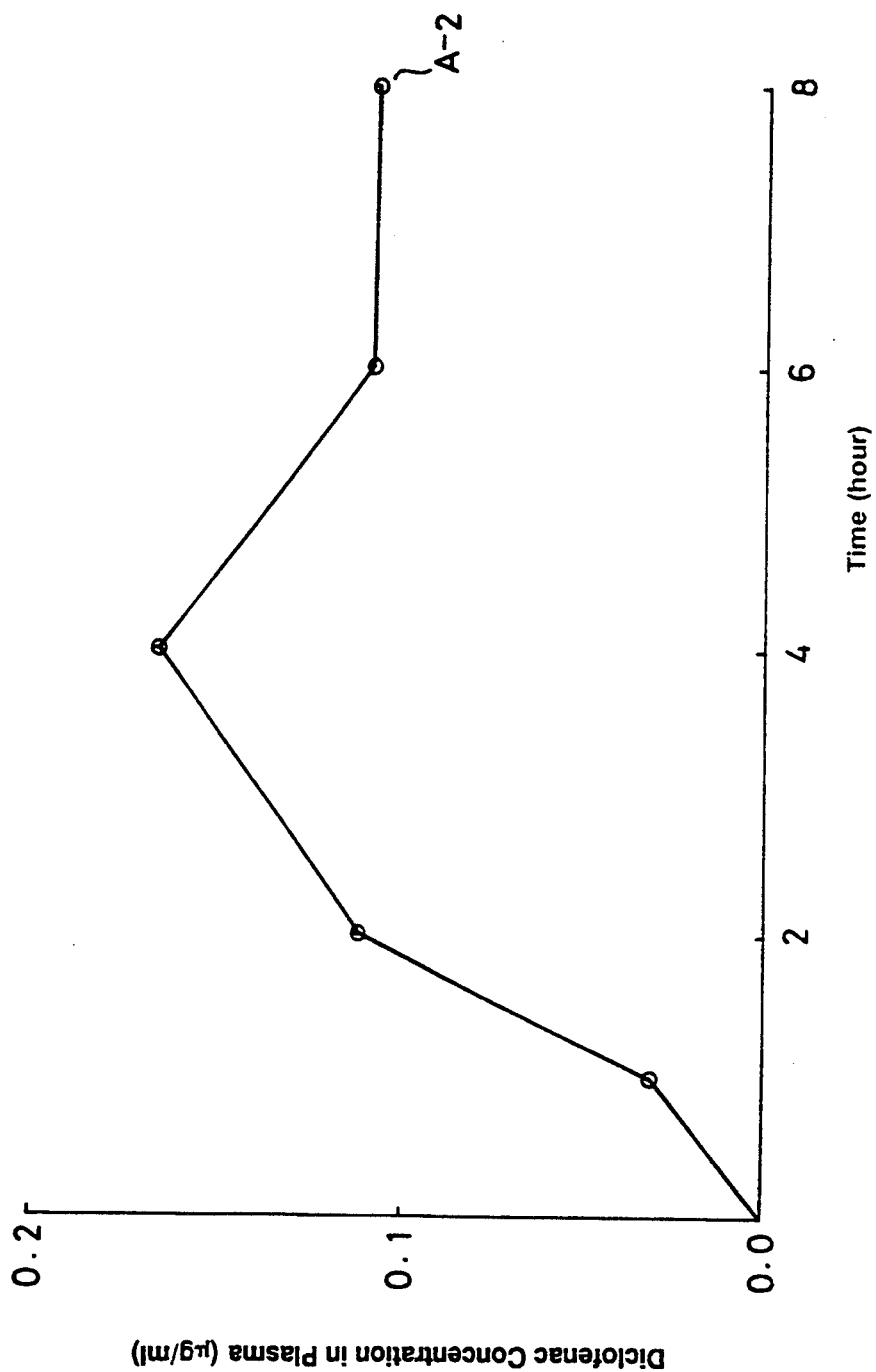
FIG. 3 shows plasma concentration of declofenac after administration of gel ointment A-2 in the back of man.

Percutaneous absorption of diclofenac through human skin was examined on 3 healthy male adults by using gel ointment A-2 of the present invention obtained in Example 1 as a sample. 7.5 g of the sample was applied to the back of the subjects by the occlusive dressing technique, and the diclofenac concentrations in plasma were measured by HPLC 1, 2, 4, 6 and 8 hours after the application. The results are shown in FIG. 3, which demonstrates excellent percutaneous absorption of diclofenac from the gel ointment of the present invention.

Test Example 7

Figure 4:
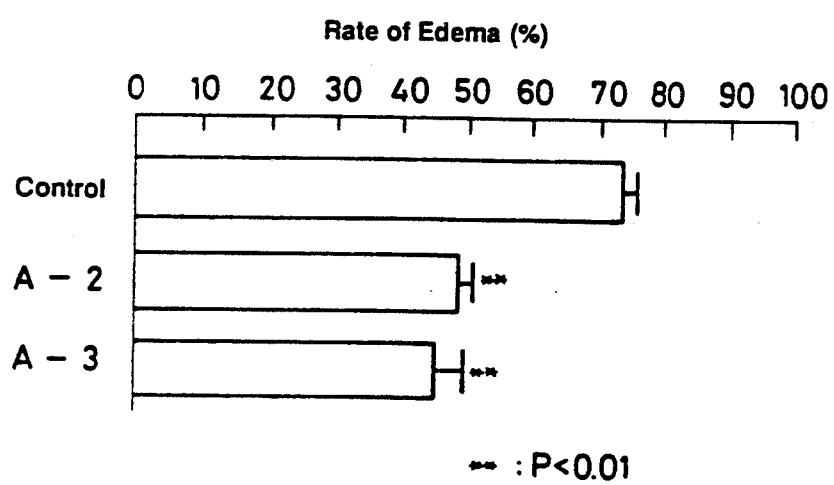
FIG. 4 shows an antiphlogistic effect of gel ointment A-2 against edema induced by carrageenan in the sole of rats.

The antiinflammatory effect of gel ointments A-2 and A-3 of the present invention obtained in Example 1 against edema induced by carrageenan in the sole of rats was examined using groups of rats, 5 rats per group. That is, 100 mg of each sample was applied to the sole of rats and wrapped for 2 hours. After 2 hours the same procedure was repeated. After 2 hours, the sample applied was removed and carrageenan was injected. After 3 hours, the volume of foot was measured to determine the degree of edema. The results are shown in FIG. 4. As cleared from FIG. 4, the degree of edema in groups to which the ointments of the present invention were applied was smaller than in the control group to which no ointment was applied, demonstrating a remarkable effect to inhibit edema induced by carrageenan.

Test Example 8

The clinical efficacy and safety of the gel ointment of the present invention was examined on orthopedic patients using gel ointment A-3 of the present invention obtained in Example 1 as a sample.

TABLE 11

| | | Remarkably Improved | Improved | Slightly Improved | No change | Slightly Impaired | Impaired | Remarkably Impaired | Total |
|---|---|---|---|---|---|---|---|---|---|
| Osteoarthritis deformans of Knee | Incidence | 0 | 7 | 3 | 0 | 0 | 0 | 0 | 10 |
| | Increment % | 0.0 | 70.0 | 100.0 | | | | | |
| Periarthritis of Shoulder | Incidence | 0 | 3 | 0 | 0 | 0 | 0 | 0 | 3 |
| | Increment % | 0.0 | 100.0 | | | | | | |
| Tendon inflammation Tendovaginitis | Incidence | 1 | 5 | 2 | 0 | 0 | 0 | 0 | 8 |
| | Increment % | 12.5 | 75.0 | 100.0 | | | | | |
| Humerus Maxillary | Incidence | 1 | 4 | 0 | 0 | 0 | 0 | 0 | 5 |
| | Increment % | 20.0 | 100.0 | | | | | | |
| Myalgia | Incidence | 1 | 0 | 1 | 0 | 0 | 0 | 0 | 2 |
| | Increment % | 50.0 | 50.0 | 100.0 | | | | | |
| Traumatic disease | Incidence | 0 | 10 | 1 | 0 | 0 | 0 | 0 | 11 |
| | Increment % | 0.0 | 90.9 | 100.0 | | | | | |
| Side effect | | not occured | Occurred | Total | | | | | |
| Incidence | | 39 | 0 | 39 | | | | | |
| Percent (%) | | 100.0 | 0.0 | | | | | | |

As clear from Table 11, the gel ointment of the present invention is excellent in both its efficacy and safety, and thus is confirmed to be useful as a pharmaceutical preparation.

Test Example 9

The safety (non-irritativeness to the skin) of the gel ointment of the present invention was compared with commercial gel ointments containing non-steroidal antiinflammatory drugs by using gel ointment A-3 as samples.

Tested compounds (about 20 mg) spread on a commercially available adhesive bandage for patch test were applied on the upper back of subjects (15 healthy male adults) for 48 hours. At 1 and 24 hours after the removal of the bandage, the degree of erythema on the site where the compounds were applied was examined and judged as light erythema (±), clear erythema (+), erythema and swelling, or papule (−), or vesicula (+).

In the test, 3 formulations consisted 1 pair, and two pairs of drugs were applied to one side of the back of the subjects (total four pairs per subject).

TABLE 12

|     | 1 hours |   |   |   | 24 hours |   |   |   |
|-----|---|---|---|---|---|---|---|---|
|     | ± | + | − | + | ± | + | − | + |
| A-3 | 4 | 1 | 0 | 0 | 2 | 2 | 0 | 0 |
| IM  | 54 | 47 | 25 | 4 | 46 | 37 | 18 | 0 |
| KP  | 10 | 1 | 1 | 0 | 26 | 17 | 1 | 0 |

IM: Indomethacin gel ointment
KP: Ketoprofen gel ointment

As shown in Table 12, it is manifest that the diclofenac sodium gel ointment of the present invention is less irritative to the skin than commercial gel ointments containing non-steroidal antiinflammatory drugs.

Industrial Applicability

The preparation comprising diclofenac or its salts of the present invention exhibits superior percutaneous diclofenac or its salts absorption, thus providing sufficient medical effects of diclofenac or its salts. In addition, the preparation is stable over time even at a high concentration of diclofenac or its salts.

What is claimed is:

1. An antiinflammatory gel preparation comprising a sodium or ammonium salt of diclofenac, a nonionic polymer, an ester of dibasic acid, and a lower alcohol.

2. The antiinflammatory gel preparation according to claim 1, wherein said nonionic polymer is one or more members selected from the group consisting of ethylcellose, hydroxyethylmethyl cellulose, hydroxypropyl cellulose, hydroxypropylmethyl cellulose, hydroxymethyl cellulose, hydroxyethyl cellulose, polyvinyl pyrrolidone, polyvinyl alcohol, and methyl cellulose.

3. The antiinflammatory gel preparation according to claim 2, wherein hydroxyethyl cellulose and hydroxypropyl cellulose are used together as nonionic polymers.

4. The antiinflammatory gel preparation according to claim 1, wherein said ester of dibasic acid is one or more members selected from the group consisting of diisopropyl adipate, diisopropyl sebacate, and diethyl sebacate.

5. The antiinflammatory gel preparation according to claim 1, wherein said lower alcohol is ethyl alcohol, isopropyl alcohol, or a mixture of these.

* * * * *

UNITED STATES PATENT AND TRADEMARK OFFICE
CERTIFICATE OF CORRECTION

PATENT NO. : 5,350,769
DATED      : September 27, 1994
INVENTOR(S) : Shuichi KASAI, et al.

It is certified that error appears in the above-indentified patent and that said Letters Patent is hereby corrected as shown below:

On the title page, Item [86], the 371 and 102(e) dates should read:

--May 14, 1992--

Signed and Sealed this

Twenty-first Day of March, 1995

Attest:

BRUCE LEHMAN

Attesting Officer     Commissioner of Patents and Trademarks